United States Patent [19]

Yudelson

[11] Patent Number: 4,672,043

[45] Date of Patent: Jun. 9, 1987

[54] STABILIZATION OF DEVELOPED ELECTROPHOREGRAMS

[75] Inventor: Joseph S. Yudelson, Rochester, N.Y.

[73] Assignee: Eastman Kodak Company, Rochester, N.Y.

[21] Appl. No.: 702,696

[22] Filed: Feb. 19, 1985

[51] Int. Cl.[4] ............................................. G01N 33/68
[52] U.S. Cl. ...................................... 436/86; 436/169
[58] Field of Search ........................... 436/86, 87, 169; 430/445, 429, 448, 413, 428

[56] References Cited

U.S. PATENT DOCUMENTS

| | | | |
|---|---|---|---|
| 2,403,927 | 7/1946 | Kendall et al. | 430/445 X |
| 3,239,340 | 3/1966 | Nasu et al. | 430/429 |
| 3,627,531 | 12/1971 | Nishio et al. | 430/448 X |
| 3,640,717 | 2/1972 | Gallet et al. | 430/413 X |
| 4,144,143 | 3/1979 | Hawkridge et al. | |
| 4,434,234 | 2/1984 | Adams et al. | |
| 4,552,848 | 11/1985 | Yudelson et al. | 436/86 |

FOREIGN PATENT DOCUMENTS

WO82/03128  9/1982  PCT Int'l Appl. .

OTHER PUBLICATIONS

U.S. Application Serial No. 495,216 (commonly assigned) filed May 16, 1983, by Yudelson et al.

Primary Examiner—Arnold Turk
Attorney, Agent, or Firm—John R. Everett

[57] ABSTRACT

In a method for determining macromolecules in polyacrylamide gels comprising the steps of forming a latent stain image by nucleating the macromolecules in the gel with a palladium tetramine salt and developing the latent stain image by treating the gel with a physical developing solution comprising dimethylamine borane and a transition metal salt, the improvement comprises contacting the developed latent stain image with a 1-phenyl-2-tetrazoline-5-thione or a salt of 1-phenyl-1H-tetrazole-5-thiol.

10 Claims, No Drawings

STABILIZATION OF DEVELOPED ELECTROPHOREGRAMS

BACKGROUND OF THE INVENTION

1. Field of the Invention

The present invention relates to an improved method for determining macromolecules such as proteins, and more particularly to a method comprising forming a latent stain image by nucleating polyacrylamide gels containing the macromolecules with a palladium tetramine salt, developing with a physical developer solution, and contacting the developed stain image with a 1-phenyl-2-tetrazoline-5-thione or a salt of a 1-phenyl-1H-tetrazole-5-thiol. 2. Description of Related Art The detection of macromolecules such as proteins and polypeptides is extremely important in many areas of biology and clinical medicine such as genetic screening and the diagnosis of genetic diseases. The primary laboratory detection and characterization technique for macromolecules is electrophoresis. Electrophoresis is the movement of charged particles in a matrix under the influence of an electric field. Continuing developments in two-dimensional gel electrophoresis have provided the capability of resolving thousands of macromolecules from complex biological mixtures.

U.S. application Ser. No. 495,216, now U.S. Pat. No. 4,552,848, of Yudelson and Johnson discloses a macromolecule electrophoregram visualization procedure of high sensitivity comprising the steps of forming a latent stain image by nucleating polyacrylamide gels containing the macromolecules with a palladium tetramine salt and developing the latent stain image by treating the gel with a specific physical developer solution.

Although this method is useful and has enjoyed widespread acceptance, the resulting developed electrophoregram is somewhat unstable (it is readily oxidized in air by the presence of moisture resulting in image loss). Reducing agents such as sodium hypophosphite have been used as image stabilizers. Such stabilizing solutions, however, require a high concentration of stabilizer compound to effect stabilization. Moreover, these stabilizing solutions fail after the supply of reducing agent is depleted by reaction with oxygen.

Example 2 of U.S. application Ser. No. 495,216 discloses a developer having therein 1-phenyl-2-tetrazoline-5-thione present at a concentration of about 0.0001%. This reference, however, does not teach or suggest the unexpected image stability resulting from the practice of this invention.

Thus, there is a need for an improved method of stabilizing developed electrophoregrams, in using electrophoregram stabilizer solutions having reduced concentration of stabilizer compound and for electrophoregrams having improved image stability.

SUMMARY OF THE INVENTION

This invention provides an improved method for visualizing macromolecules in electrophoregrams comprising the steps of forming a latent stain image by nucleating the macromolecules in the polyacrylamide gel with a palladium tetramine salt and developing the latent stain image with a physical developer solution comprising dimethyl amine borane and a member selected from the group consisting of a transition metal salt and a tetrazolium salt wherein the improvement comprises stabilizing the developed latent stain image by contacting the gel with a 1-phenyl-2-tetrazoline-5-thione or a salt of a 1-phenyl-1H-tetrazole-5-thiol.

An electrophoregram that consists of a polyacrylamide slab is visualized by nucleation with a palladium tetramine salt, developed in a physical developer comprising dimethylamine borane, a member selected from the group consisting of transition metal salt and a tetrazolium salt and optionally an antifoggant, and stabilized by contacting the developed image with a salt of a 1-phenyl-1H-tetrazole-5-thiol or a 1-phenyl-2-tetrazoline-5-thione.

Kits comprising a palladium tetramine salt, dimethylamine borane, a developer member selected from the group consisting of a transition metal salt and a tetrazolium salt and the aforementioned stabilizer compound used in this method are also described. Use of these kits can find utility in clinical and laboratory examination of blood and other macromolecules separable by electrophoresis, diagnosis of fetal abnormalities by examination of amniotic fluid, diagnosis of central nervous system disease by analysis of macromolecule patterns in spinal fluid and other applications in which the detection and/or quantitation of macromolecules is desired.

The electrophoregram images stabilized by the method of this invention are extremely stable and can be stored for weeks or longer without significant image loss. Further, the concentration of stabilizer required to effect image stabilization is extremely low.

DESCRIPTION OF PREFERRED EMBODIMENTS

The macromolecules to be detected in this invention are preferably proteins, although other macromolecules such as nucleic acids and polypeptides can be detected by the present improved method.

The electrophoretic separation using polyacrylamide gel slabs is carried out using any of the procedures well known in the art. Such procedures are described in U.S. application Ser. No. 495,216 noted above, the disclosure of which is hereby incorporated by reference in its entirety.

In the preferred embodiments of this invention, the stabilizing compound which is a 1-phenyl-2-tetrazoline-5-thione or a 1-phenyl-1H-tetrazole-5-thiol salt is present in solution at 0.005 to 0.5% by weight of the solvent. Useful herein are the unsubstituted forms of these compounds:

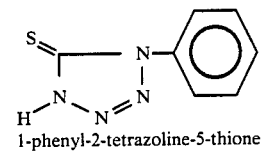

1-phenyl-2-tetrazoline-5-thione

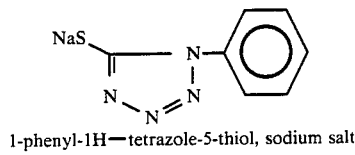

1-phenyl-1H—tetrazole-5-thiol, sodium salt and substituted forms of these compounds, for example, such compounds having the phenyl group substituted with groups such as lower alkyl such as methyl and ethyl and the like, provided that the solubility of the substituted stabilizing compound remains sufficient to provide for a 0.005–0.5% solution and that good stabilizing characteristics are retained.

The solvent is one in which the stabilizer is soluble, preferably water. Mixtures of solvents may also be used to advantage. For example, the solubility of the stabilizer in aqueous solution may be enhanced by the addition of methanol. Other useful solvents besides water include methyl alcohol, ethyl alcohol, acetonitrile and the like.

The preferred 1-phenyl-1H-tetrazole-5-thiol salt is the sodium salt having been found to possess excellent solubility and stabilizing characteristics. However, other such unsubstituted and substituted salts including the potassium salts are also useful herein.

Electrophoregram visualization includes the step of forming a latent stain image by nucleating the macromolecules in the gel with a palladium tetramine salt such as palladium tetramine chloride, palladium tetramine nitrate, palladium bis(ethylene diamine) chloride or potassium palladium tetrathiocyanate. Palladium tetramine chloride and palladium tetramine nitrate yield excellent results in that they possess the proper combination of stability and solubility to sensitize the macromolecular area from the electrophoregram. Optionally, sodium dodecyl sulfate (SDS) sensitizer can be combined with the palladium tetramine salt in one solution or can be present in separate solutions. The palladium tetramine salt nucleator is generally present in coverages of from about 0.009 to 1.9 mg/m$^2$.

The development of the latent stain image is accomplished by treating the gel with a developer solution comprising dimethylamine borane as the reducing agent. The reducing agent can be present in amounts between about 1 mg/0.093 m$^2$ and about 200 mg/0.093 m$^2$. The developer solution also comprises a transition metal salt or tetrazolium salt physical developer. The transition metal salt or tetrazolium salt can be present in the amounts between about 1 mg/0.093m$^2$ and about 100 mg/0.093m$^2$.

A variety of tetrazolium salts may be used in the practice of the present invention. It is understood that the term "tetrazolium salt" throughout the application includes tetrazolium salts, ditetrazolium salts and tetrazolium betaines, and other reducible dye precursors.

Useful tetrazolium salts are described in "The Chemistry of Formazans and Tetrazolium Salts", A. W. Nineham, Chem. Rev., 55, 355 (1955) hereby incorporated by reference. The synthesis of tetrazolium salts and the chelation of formazan dyes are also described in the above reference.

Tetrazolium salts useful in the present invention include compounds having the general formula:

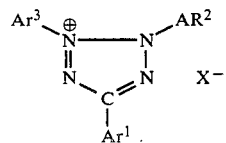

wherein Ar$^1$, Ar$^2$ and Ar$^3$ may be the same or different and represent phenyl groups or phenyl groups substituted with electron withdrawing groups such as nitro, methoxy and the like or electron donating groups such as alkyl; and Ar$^3$ can also represent a 4,5-dialkyl-2-thiazolyl group containing 1 to 5 carbon atoms in the alkyl group or a 2-benzthiazolyl group; and X$^-$ is an anion such as halide, acetate, tetrafluoroborate and the like.

Specific examples of tetrazolium salts and methods for their preparation can be found in Canadian Patent No. 860,873, which is hereby incorporated by reference.

Triazolium salts may also be employed as redicible dye precursors in the practice of this invention. These are colorless compounds that are reduced by the process of the invention to colored azo-amine dyes. Exemplary triazolium salts are disclosed in Research Disclosure, Item No. 12617, Vol. 126, October 1974 at Table IV.

Physical developer baths can be made from substantially equal volumes of a solution of a tetrazolium salt and a solution of a reducing agent. The resulting physical developer bath is considered useful if the tetrazolium salt is not spontaneously reduced to formazan dye but is reduced to formazan dye when palladium (O) or other catalyst is added to the bath. By spontaneously, it is meant that the formazan dye is formed essentially instantaneously without the metal nuclei.

The physical developers useful in the present invention can be simple solvent solutions of the tetrazolium salt and the reducing agent. The solvent is one in which the tetrazolium salt is soluble and the corresponding formazan dye as well as the palladium nuclei is insoluble. Mixtures of solvents may also be used to advantage. For example, the solubility of a tetrazolium salt in aqueous solution may be enhanced by the addition of methanol. Other useful solvents besides water include methyl alcohol, ethyl alcohol, acetonitrile and the like.

The solution can be saturated with the tetrazolium salt but is useful with as little as about 0.1% tetrazolium salt by weight of the solvent.

The transition metal salt deposited from the developer bath must itself be autocatalytic; that is, it must act as a catalyst for further deposition of metal from the developer. This is necessary in order that deposition and development will continue after palladium nuclei are enveloped with heavy metal. With respect to the Periodic Table, suitable heavy metals can be selected from Group VIII metals such as nickel, cobalt, iron, palladium and platinum, Group VIB metals such as chromium and Group IB metals such as copper, silver and gold. Almost any heavy metal salt which is a source of the desired heavy metal ions can be employed. Suitable heavy metal salts useful in the invention include heavy metal halides such as cobaltous bromide, cobaltous chloride, cobaltous iodide, ferrous bromide, ferrous chloride, chromium bromide, chromium chloride, chromium iodide, copper chloride, silver bromide, silver chloride, silver iodide, gold chloride, palladium chloride and platinum chloride, heavy metal sulfates such as nickel sulfate, ferrous sulfate, cobaltous sulfate, chromium sulfate, copper sulfate, palladium sulfate and platinum sulfate, heavy metal nitrates such as nickel nitrate, ferrous nitrate, cobaltous nitrate, chromium nitrate and copper nitrate, and heavy metal salts of organic acids such as ferrous acetate, cobaltous acetate, chromium acetate and copper formate. Baths can be formulated based on a single heavy metal or based on mixtures of heavy metals.

The developer solution also preferably contains an antifogging agent to reduce the effects of fogging. It has been found that ethyl cysteine HCl, or dimethyl cysteine dihydrochloride in combination with the dimethylamine borane yields excellent discrimination between image and background. Other antifoggants such as dimethylaminoethanethiol HCl are also useful herein.

In the preferred embodiments of this invention, the physical development bath contains from 0.1% to 10% of the dimethylamine borane, from 0.1% to 10% of the transition metal salt or tetrazolium salt and from about 0.01% to 1% of the antifoggant.

The physical developer solution can contain additional materials such as complexing agents such as gluconic acid, tartaric acid, citric acid and ethylene diamine tetraacetic acid. It has been found that the use of gluconic acid produces superior results in sensitivity, stability and fog levels.

In addition, it is desirable to include SDS sensitizer in the physical developer solution. Thus, amounts of 0.1% to 1% of SDS in the developer solution result in greater sensitivity without excessive fogging. The development is generally carried out in 10 to 30 minutes.

After development is completed, the developed electrophoregram is contacted with a 1-phenyl-2-tetrazoline-5-thione or a salt of 1-phenyl-1H-tetrazole-5-thiol. To prevent image loss for extended periods of time, subsequent to the development stage the developed electrophoregram preferably is immersed and stored in the stabilizer solution.

Kits comprising a palladium tetramine salt, dimethylamine borane, an antifoggant, a developer member selected from the group consisting of a transition metal salt and a tetrazolium salt and a stabilizer are useful in using electrophoregrams.

The following examples are presented to illustrate more fully the invention.

EXAMPLE 1

Preparation of Developed Electrophoregrams

A developer was prepared as follows:

| Solution A | |
|---|---|
| $NiCl_2 \cdot 6H_2O$ | 36 g |
| Sodium gluconate | 109 g |
| Dilute to 1 liter, adjust pH to 7.0 with concentrated NaOH | |
| Solution B | |
| Dimethylamine borane | 3% (aq) |
| Solution C | |
| Ethyl cysteine HCl | 1% (aq) |

The solutions were mixed as follows:

| Solution A | 40 ml |
|---|---|
| Solution B | 10 ml |
| Solution C | 0.01 ml |
| Water | 55 ml |

A sensitizer $Pd(NH_3)_4Cl_2$ was prepared as follows: 3.6 gm of $PdCl_2$ was mixed with 350 ml of deionized water and 50 ml of concentrated ammonium hydroxide. After stirring overnight, all of the $PdCl_2$ had dissolved. This solution was placed under aspirator vacuum for 8 hours and diluted to 500 ml with water to give a 1% solution of $Pd(NH_3)_4Cl_2$ whose final pH was 8.7.

An electrophoregram of B-Galactosidase in polyacrylamide gel (0.75 mm thick) containing 10% acrylamide and 2.7% methylene bisacrylamide were fixed in $CH_3OH$—$H_2O$ (1:1) for at least one hour and then sensitized as follows:

| 1. Rinse in deionized water | 1 min. |
|---|---|
| 2. Sodium Dodecyl Sulfate (2%) | 1 min. |
| 3. Water | 2 min. |
| 4. Nucleated $Pd(NH_3)_4Cl_2$ (0.15%) | 1 min. |
| 5. Rinse (deionized water) | 1 min. |

The electrophoregram was developed in the solution for 20 minutes at 25° C. After this time, the main protein band could be observed at low protein concentrations.

Following development, the electrophoregrams of this example were washed for 1 minute in two changes of distilled water and stored under the following two sets of conditions:

| (1) Water | |
|---|---|
| (2) 1-phenyl-2-tetrazoline-5-thione | 0.05% |

After a few days storage at room temperature, Sample #1 showed severe image loss whereas the sample stored in the 1-phenyl-2-tetrazoline-5-thione containing stabilizer solution showed no image loss after several weeks aging.

EXAMPLE 2

Effect of Stabilization

Following development, the electrophoregrams of Example 1 were immersed in the following stabilizing solutions;

| (1) Sodium hypophosphite | 10% |
|---|---|
| (2) 1-phenyl-1H-tetrazole-5-thiol sodium salt | 0.1% | and dried by standard techniques on a Hoefer slab gel dryer.

The electrophoregram stabilized in sodium hypophosphite turned appreciably darker upon drying whereas the electrophoregram stabilized in the 1-phenyl-1H-tetrazole-5-thiol salt solution evidenced no image loss throughout the drying procedure.

The invention has been described in detail with particular reference to preferred embodiments thereof, but it will be understood that variations and modifications can be effected within the spirit and scope of the invention.

What is claimed is:

1. In a method for determining macromolecules in polyacrylamide gels, said method comprising the steps of
    (a) forming a latent stain image by nucleating the macromolecules in the gel with a palladium tetramine salt and
    (b) developing the latent stain image by treating the gel with a physical developer solution comprising dimethylamine borane and a member selected from the group consisting of a transition metal salt and a tetrazolium salt,
    (c) rinsing off the developing solution,
wherein the improvement comprises subsequently stabilizing the developed latent stain image by contacting the gel with a stain stabilizing amount of a 1-phenyl-2-tetrazoline-5-thione or a salt of a 1-phenyl-1H-tetrazole-5-thiol.

2. The method of claim 1 wherein the stabilizer is present in solution at 0.005 to 0.5%.

3. The method of claim 1 wherein said transition metal is nickel.

4. The method of claim 2 wherein said stabilizing solution comprises 1-phenyl-1H-tetrazole-5-thiol sodium salt.

5. The method of claim 1 wherein said palladium salt is palladium tetramine chloride.

6. In a method for determing macromolecules in polyacrylamide gels, said method comprising in order the stages of
   (a) a nucleating stage comprising forming a latent stain image by nucleating the macromolecules in the gel with a palladium tetramine salt,
   (b) a developing stage comprising developing the latent stain image by treating the gel with a physical developer solution comprising dimethylamine borane and a member selected from the group consisting of a transition metal salt and a tetrazolium salt,
   (c) rinsing off the developing solution, wherein the improvement comprises after the rinsing stage,
   (d) a stabilizing stage comprising contacting the gel with a stabilizer solution comprising a stain stabilizing amount of a 1-phenyl-2-tetrazoline-5 thione or a salt of a 1-phenyl-1H-tetrazole-5 thiol.

7. The method of claim 6 wherein the stabilizer is present in solution at 0.005 to 0.5%.

8. The method of claim 6 wherein said transition metal is nickel.

9. The method of claim 6 wherein said stabilizer is 1-phenyl-1H-tetrazole-5-thiol sodium salt.

10. The method of claim 6 wherein said palladium salt is palladium tetramine chloride.

* * * * *